United States Patent [19]

Tyrrell et al.

[11] Patent Number: 5,039,667

[45] Date of Patent: Aug. 13, 1991

[54] ANTIVIRAL THERAPY FOR HEPATITIS B WITH 2',3'-DIDEOXYPURINE NUCLEOSIDES

[75] Inventors: David L. J. Tyrrell, Edmonton, Canada; Morris J. Robins, Provo, Utah; Satoru Suzuki, Hokkaido, Japan

[73] Assignee: The Governors of the University of Alberta, Edmonton, Canada

[21] Appl. No.: 228,745

[22] Filed: Aug. 5, 1988

Related U.S. Application Data

[63] Continuation-in-part of Ser. No. 178,196, Aug. 7, 1987, abandoned.

[51] Int. Cl.$^5$ .................. A61K 31/70; C07H 19/16; C07H 19/173
[52] U.S. Cl. .................................... 514/45; 514/46; 536/24; 536/26; 424/43; 424/433; 424/436; 424/464
[58] Field of Search .............. 536/26; 514/46; 424/43, 424/433, 436, 464

[56] References Cited

FOREIGN PATENT DOCUMENTS

0206497 12/1986 European Pat. Off. .............. 536/26
WO90/14079 5/1989 PCT Int'l Appl. .
WO90/14091 5/1989 PCT Int'l Appl. .

OTHER PUBLICATIONS

Miller et al., "Hepatitis B Virus Particles of Plasma and Liver Contain Viral DNA-RNA Hybrid Molecules," Virology (1984), 139:53-63.

Wagar et al., "Effects of 2',3'-Dideoxynucleosides on Mammalian Cells and Viruses," J. Cell. Physiol. (1984), 121:402-408.

Tsiquaye et al., "Suramin Inhibits Duck Hepatitis B Virus DNA Polymerase Activity," J. Hepatol. (1985), 1:663-669.

Lien et al., "Initiation and Termination of Duck Hepatitis B Virus DNA Synthesis During Virus Maturation," J. Virol. (1987), 61:3832-3840.

Will et al., "Replication Strategy of Human Hepatitis B Virus," J. Virol. 61:904-911.

Loke et al., "Suramin Treatment for Chronic Active Hepatitis B—Toxic and Ineffective," J. Med. Virol. (1987), 21:97-99.

Haritani et al., "Effect of 3'-Azido-3'-Deoxythymidine on Replication of Duck Hepatitis B Virus in vivo and in vitro," J. Med. Virol. (1989), 29:244-248.

Farraye et al., "Preliminary Evidence that Azidothymidine Does Not Affect Hepatitis B Virus Replication in Acquired Immunodeficiency Syndrome (AIDS) Patients," J. Med. Virol. (1989), 29:266-267.

Ueda et al., "Short Communications: An in vitro System for Screening Anti-Hepatitis B Virus Drugs," Virol. (1989), 169:213-216.

Kassianides et al., "Inhibition of Duck Hepatitis B Virus Replication by 2',3'-Dideoxycytidine," Gastroenterol. (1989), 97:1275-1280.

(List continued on next page.)

Primary Examiner—Ronald W. Griffin
Assistant Examiner—L. Eric Crane
Attorney, Agent, or Firm—Banner, Birch, McKie & Beckett

[57] ABSTRACT

A method is disclosed for the treatment of hepadnavirus infection in animals. Animals infected with duck hepatitis B virus may be treated with the 2',3'-dideoxynucleoside of adenine, guanine, hypoxanthine, 2,6-diaminopurine or various analogs of substituted purines. Several purine 2',3'-dideoxynucleosides inhibit duck hepatitis B virus in hepatocyte culture >99% at 1 μg/ml. Potent in vivo efficacy of the 2,6-diaminopurine 2',3'-dideoxynucleoside for clearance of duck hepatitis B virus from the sera of Pekin ducks is demonstrated. The selective effect on hepadnavirus replication by the purine 2',3'-dideoxynucleosides is based on the discovery of an unexpected sensitivity of hepadnavirus to purine 2',3'-dideoxynucleoside analogs. These compounds present a new antiviral therapy of acute or persistent hepadnavirus infections.

30 Claims, 4 Drawing Sheets

DOSAGE RESPONSE CURVES OF DIDEOXYNUCLEOSIDES

OTHER PUBLICATIONS

Lee et al., "In vitrol and In vivo Comparison of the Abilities of Purine and Pyrimidine 2',3'-Dideoxynucleosides to Inhibit Duck Hepadnavirus," Antimicrob. Agents and Chemother. (1989), 33:336–339.

Suzuki et al., "Inhibition of Duck Hepatitis B Virus Replication by Purine 2',3'-Dideoxynucleosides," Biochem. and Biophys. Res. Comm. (1988), 156:1144–1151.

Tiollais et al., "The Hepatitis B Virus," Nature (1985), 317:489–495.

Zukerman, "Screening of Antiviral Drugs for Hepadna Virus Infection in Pekin Ducks: A Review," J. Virol. Meth. (1987), 17:119–126.

DOSAGE RESPONSE CURVES OF DIDEOXYNUCLEOSIDES

ANTIVIRAL THERAPY FOR HEPATITIS B WITH 2',3'-DIDEOXYPURINE NUCLEOSIDES

This is a continuation-in-part of application Ser. No. 178,196, filed Aug. 7, 1987, now abandoned.

FIELD OF THE INVENTION

This invention relates to a method of using purine 2',3'-dideoxynucleosides or pharmaceutically acceptable derivatives thereof as antiviral therapy in the treatment of acute or chronic hepatitis B virus infection in animals.

BACKGROUND OF THE INVENTION

Hepatitis B is a common disease with a worldwide distribution. The virus is transmitted by blood and blood products, contamination of needles in IV drug abusers, sexually and vertically from infected or carrier mothers to infants. On a global basis, the disease is most common in Southeast Asia, Africa and parts of South America. In these areas, vertical transmission to infants at an early age results in a high proportion of infected individuals becoming chronic carriers of hepatitis B. Males acquiring hepatitis B as infants have approximately a 40% chance of dying from cirrhosis or primary hepatocellular carcinoma as a result of chronic hepatitis B infection. Females infected at birth have about a 15% chance of dying a similar death from chronic hepatitis B infection. It is estimated that there are 280,000,000 carriers of hepatitis B worldwide.

The field of antiviral chemotherapy is relatively new. Since the replication of viruses so intimately involves the host cell, it has been very difficult to identify viral specific sites for specific antiviral chemotherapy. Attempts to treat chronic carriers of hepatitis B have met with little success. Adenine arabinoside and inteferon have been used to treat chronic carriers. There have been three controlled studies comparing adenine arabinoside to a placebo in the treatment of chronic hepatitis B infection. In two of these studies, the response rate to adenine arabinoside was significantly better in treated patients than in controls (Bassendine et al, *Gastroenterology*, 80, 1016–1021, 1981; Yokosuta et al *Gastroenterology*, 89, 246–251, 1985). In a third controlled study, there was no significant benefit in the adenine arabinoside treated patients (Hoofnagle et al, *Gastroenterology*, 86, 150–157, 1984). Priming the patients with a tapering course of prednisone before therapy with adenine arabinoside has been reported to be beneficial (Perrillo, R. P. et al, *Gastroenterology*, 88, 780–786, 1985). However, in most open and controlled studies, only about 30% of treated patients show some benefit from therapy, and even these results are not very convincing. In addition, therapy with adenine arabinoside has been associated with bone marrow suppression, neuromuscular pain and neurotoxicity. Most trials of adenine arabinoside for the treatment of chronic hepatitis B infection have been discontinued because of the limited success and moderate toxicity with this antiviral agent. Attempts to treat chronic active hepatitis caused by hepatitis B virus with interferon alone or in combination with adenine arabinoside have also met with very limited success and considerable toxicity. Thus there is a lack of effective antiviral treatment for hepatitis B.

The 2',3'-dideoxynucleosides have been proposed as antiviral agents and, in fact, 2',3'-dideoxycytidine is being actively investigated as an antiviral agent for retroviruses including the human immunodeficiency viruses (HIV). Other 2',3'-dideoxynucleosides but not 2',3'-dideoxythymidine have been shown to be potent inhibitors of HIV (Mitsuya et al *PNAS* 82, 7096–7100, 1985; Mitsuya and Broder, *PNAS* 83, 1911–1915, 1986).

Burroughs Wellcome disclose in their published European patent application S.N. 8603662.0 that the dideoxynucleosides may be useful in the treatment of hepadnavirus infections like hepatitis B. However, they provide no experimental evidence to support this hypothesis and do not mention our unexpected finding that purine 2',3'-dideoxynucleosides are much more effective than pyrimidine 2',3'-dideoxynucleosides. Although 2',3'-dideoxynucleosides are known to have antiviral activity, the work disclosed has concentrated on this type of compound as being effective for retroviruses, specifically HIV. The most effective 2'3' dideoxynucleosides for HIV have been 2'3'-dideoxycytidine (ddC) and 2',3'-dideoxyadenosine (ddA), a pyrimidine 2',3'-dideoxynucleoside and a purine 2',3'-dideoxynucleoside, respectively. Obviously, it is impossible to predict the qualitative sensitivities of the hepadnaviruses to 2',3'-dideoxynucleosides based on known sensitivities of retroviruses to these compounds. This is not surprising since retroviruses are RNA viruses whereas hepadnaviruses are DNA viruses of a distinctly different family and replicate by a different mechanism.

SUMMARY OF THE INVENTION

According to an aspect of the invention, a method for medically treating animals infected with a hepadnavirus comprises administering to such animal a formulation comprising an efficacious amount of a biologically active 2',3'-dideoxynucleoside in conjunction with a biologically compatible carrier, said 2',3'-dideoxynucleoside being represented by the formula:

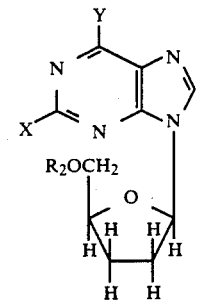

wherein
X is H, $R_1$, $NH_2$, halogen, $NHR_1$, $N(R_1)_2$, OH, $OR_1$, SH, or $SR_1$,
Y is H, $R_1$, $NH_2$, halogen, $NHR_1$, $N(R_1)_2$, OH, $OR_1$, SH, or $SR_1$,
$R_1$ is a lower alkyl group of 1 to 8 carbon atoms, and,
$R_2$ is H or a biologically compatible ester or salt of said ester to provide a biologically compatible salt.

BRIEF DESCRIPTION OF THE DRAWINGS

Preferred embodiments of the invention are shown in the drawings wherein.

DETAILED DESCRIPTION OF THE PREFERRED EMBODIMENTS

Figure 1:
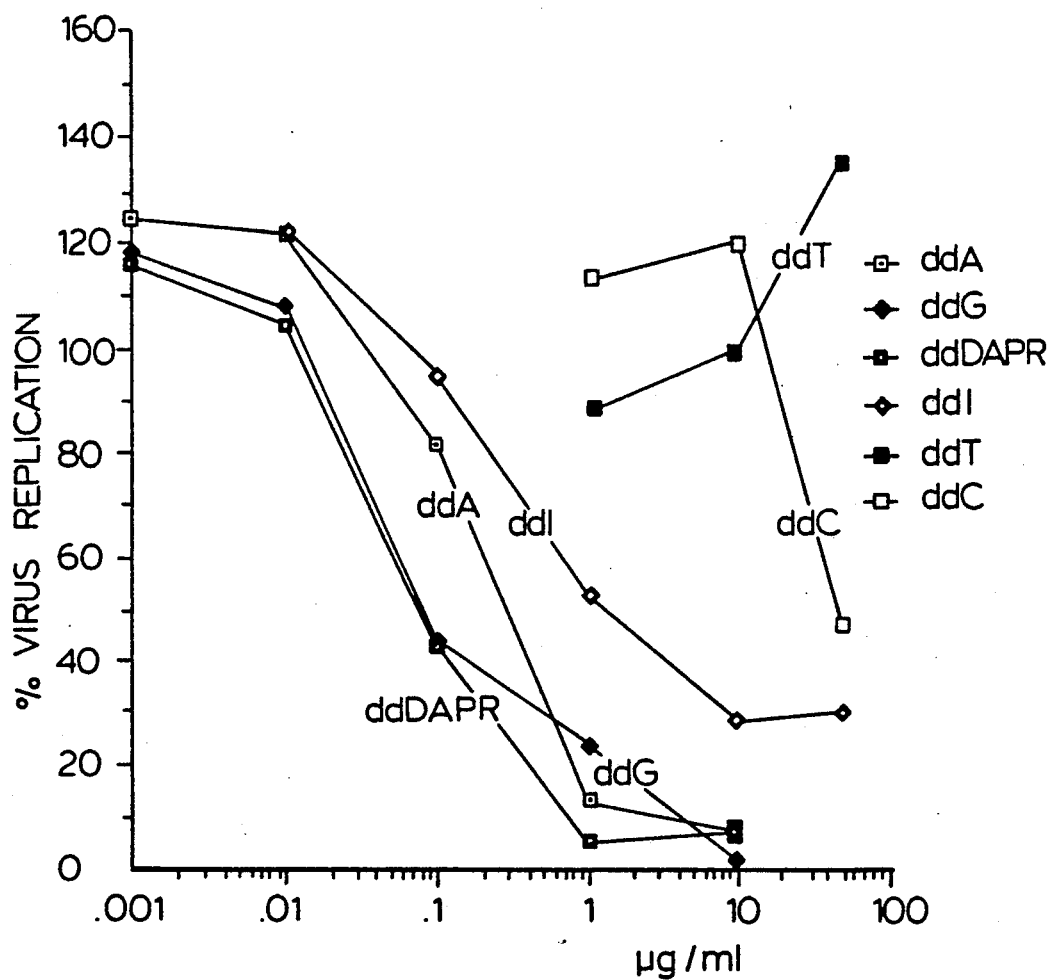
FIG. 1 shows the dose response curves for selected purine and pyrimidine 2',3'-dideoxynucleosides.

The discovery that the compounds of Formula I have unexpected significant utility as antiviral agents in the treatment of hepadnavirus infections is demonstrated in this detailed discussion of the preferred embodiments of the invention. It is appreciated that the efficacy of such compounds is most readily demonstrated in animals and in particular, it is well known that the duck hepatitis B virus behaves very similarly in ducks as the analogous hepatitis B virus behaves in humans. Hence, testing of these compounds to prove their unexpected utility has been carried out in ducks infected with the duck hepatitis B virus (DHBV). It is appreciated that the compounds are effective in animals infected with hepadnaviruses; for example, human and non-human animals. Non-human animals include ducks, woodchucks, small Beechey ground squirrels and kangaroos.

In past studies of antiviral agents, no distinction has been made between the activities of purine 2',3'-dideoxynucleosides and pyrimidine 2'3'-dideoxynucleosides. Such distinction in activities has been clearly demonstrated in the present system for the duck hepatitis B virus. The basis for the selective antiviral activity of purine 2',3'-dideoxynucleoside is not fully understood. It is presently postulated that the compounds of Formula I have the ability to bind the genome-linked protein which primes the synthesis of the negative strand of DNA. Since the completed negative strand serves as a template for the synthesis of the positive strand (Will et al, *J. of Virology*, 61, 904-911 1987), blockage at this early stage of DNA synthesis would block the synthesis of both negative and positive DNA strands.

The replication of hepadnaviruses differs markedly from that of other DNA viruses. A major difference is a reverse transcription step analogous to that seen in retroviruses. The replication mechanism for hepadnaviruses was initially discovered in the DHBV model by Summers and Mason (*Cell* 29, 403-415 1982; Mason et al *PNAS*, USA, 3997-4001, 1982) and later shown to be similar in hepatitis B (Blum et al, *Virology* 139, 87-96, 1984; Miller et al *Virology*, 139, 53-63, 1984; Miller et al *Virology*, 139, 64-72, 1984).

After the hepadnavirus penetrates the target cells (hepatocytes), the virus is uncoated and the DNA enters the nucleus. In the nucleus, the partially double stranded-DNA of the virus is converted to a double stranded covalently closed circular form. The negative strand acts as the template for synthesis of pregenomic RNA which is larger (3.4 kb) than the negative strand (3.2 kb). The pregenomic RNA is synthesized by cellular RNA polymerase. The pregenomic RNA serves as the template for the negative strand DNA synthesis which is accomplished by the viral DNA polymerase (reverse transcriptase activity). The synthesis of the negative strand is primed by a covalently-linked protein (Gerlich and Robinson, *Cell* 21, 801-809, 1980; Molnar-Kimber et al, *J. of Virology*, 45, 165-172, 1984). During the synthesis, the pregenome RNA is degraded by the ribonuclease H-like activity of the viral DNA polymerase. At the completion of the negative strand synthesis, a small piece of the pregenomic RNA is transposed from the DR1 to the DR2 region of minus strand and serves as the primer for the positive strand synthesis (Will et al, *J. of Virology*, 61, 904-911, 1987). The synthesis of the positive strand may not be completed before coating by nucleocapsids and export of viral particles.

Hence, a possible explanation of the unexpected sensitivity of hepadnaviruses to purine 2'3'-dideoxynucleosides compared to pyrimidine 2'3'-dideoxynucleosides is that the purine 2'3'-dideoxynucleosides bind to the genome-linked protein which primes the negative strand synthesis. In the hepatitis B virus, the 5' end of the negative strand sequence is 5'-d(GAAAAAGT...) (Will et al *J. of Virology*, 61, 904-911 1987) and 5'-d(GTAATTCTT...) in DHBV (Lien, J. M. et al *J. of Virology*, 61, 3832-3840, 1987). In both instances, the nucleotide at the 5'end which links to the protein is a purine nucleotide. The present results in hepatocyte cultures indicate that DHBV, and by analogy the other hepadnaviruses, are at least 100 to 1000 times more sensitive to purine 2',3'-dideoxynucleoside than pyrimidine 2'3'-dideoxynucleosides. This unique step of protein priming of the negative strand of DNA synthesis is a possible mechanism by which this unexpected finding might be explained. It is appreciated, however, that other mechanisms may be at work. In any event, the test results clearly demonstrate the effectiveness of the compounds of Formula I.

The unexpected sensitivity of hepadnaviruses to purine 2',3'-dideoxynucleosides without any apparent adverse effect on host cells at much higher concentrations (100 to 1000 fold) suggests that these antiviral agents are acting at a unique step in viral replication. The hypothesis that the protein priming of the viral nucleic acid synthesis is blocked by purine 2',3'-dideoxynucleosides has widespread application for other viruses such as polio and adenoviruses which are also known to have protein priming of their nucleic acid synthesis.

The compounds which are useful in this invention are represented by the following Formula I:

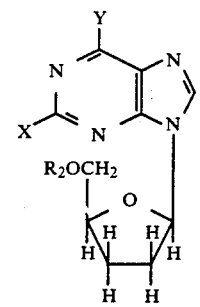

In this Formula, X is H, $R_1$, $NH_2$, halogen, $NHR_1$, $N(R_1)_2$, OH, SH, $OR_1$ or $SR_1$; Y is H, $R_1$, $NH_2$, halogen, $NHR_1$, $N(R_1)_2$, OH, SH, $OR_1$ or $SR_1$; $R_1$ is a lower alkyl group of 1 to 8 carbon atoms and $R_2$ is H or a biologically compatible ester or salt of said ester to provide a biologically compatible salt.

Representative compounds of the above Formula are set out in the following Table 1.

TABLE 1

| X | Y |
|---|---|
| 1. H | OH |
| 2. H | $NH_2$ |
| 3. R (R = $CH_3$, $C_2H_5$, etc) | $NH_2$ |

TABLE 1-continued

| X | Y |
|---|---|
| 4. $NH_2$ | OH |
| 5. $NH_2$ | OR (R = $CH_3$, $C_2H_5$, etc) |
| 6. $NH_2$ | $NH_2$ |
| 7. $NH_2$ | H |
| 8. $NH_2$ | SH |
| 9. $NH_2$ | NHR (R = $CH_3$, $C_2H_5$ etc.) |
| 10. $NH_2$ | $N(R)_2$ (R = $CH_3$, $C_2H_5$ etc.) |
| 11. $NH_2$ | Halogen (F, Cl, Br, I) |
| 12. $NH_2$ | SR (R = $CH_3$, $C_2H_5$ etc.) |
| 13. Halogen (F, Cl, Br, I) | $NH_2$ |
| 14. NHR (R = $CH_3$, $C_2H_5$ etc.) | $NH_2$ |
| 15. $N(R)_2$ (R = $CH_3$, $C_2H_5$ etc.) | $NH_2$ |
| 16. OH | $NH_2$ |
| 17. OR (R = $CH_3$, $C_2H_5$, etc) | $NH_2$ |
| 18. SH | $NH_2$ |
| 19. SR (R = $CH_3$, $C_2H_5$ etc.) | $NH_2$ |

The preferred compounds of Formula 1 are the adenine, guanine, hypoxanthine or 2,6-diaminopurine derivatives of the above Formula; i.e. wherein X is H and Y is $NH_2$, X is $NH_2$ and Y is OH, X is H and Y is OH and X is $NH_2$ and Y is $NH_2$, respectively. Many of the above compounds of Table 1 function as pro-drugs which in vivo are metabolized to the more active 2',3'-dideoxynucleosides such as 2',3'-dideoxyguanosine.

$R_2$ may be H to form hydroxyl or an acyl group which forms esters thereof, salts of the esters or salts per se, all of which are biologically compatible. Such ester may be straight or branched chain. Preferably, the ester is of lower chain length having 1 to 4 carbon atoms. One or more of the compounds may be administered to provide an efficacious concentration in the blood stream of less than 50 µg/ml. The preferred concentration range for dosage is in the range of 0.1 to 10.0 µg/ml. Such compositions may be administered by normal procedures such as oral tablets, liquid, suppository, injectable liquid, aerosol, etc.

The absence of an effective antiviral agent for the treatment of hepatitis B prompted the use of duck hepatocyte cultures to grow DHBV and to test chemotherapeutic agents for antiviral activity. Duck hepatocyte cultures are used to grow DHBV and to test chemotherapeutic agents for antiviral activity. Although the methods outlined discuss treatment of DHBV, it is understood that this method of treatment is effective against viruses that replicate via a similar mechanism. The following examples are therefore intended to demonstrate various aspects of the invention without being limiting to the scope of the invention as defined in the appended claims.

Dose response curves for the purine 2',3'-dideoxynucleosides and pyrimidine 2',3'-dideoxynucleosides have been established by using the duck hepatitis B virus (DHBV) infected hepatocyte system. The DHBV-infected hepatocyte cultures were established as described in Example 1. Dideoxynucleoside analogs were added to the media of the hepatocyte cultures on day 2 and maintained in culture with media changes every two days. On day sixteen the DNA was extracted from the cells and the dot blots performed using the $^{32}P$-labelled DHBV probe. The radioactivity of each "dot" was quantitated by cutting out the "dot" and counting the radioactivity. The abbreviations used in FIG. 1, setting out the dose response curves, are as follows:
ddA = 2',3'-dideoxyadenosine:
ddG = 2',3'-dideoxyguanosine;
ddDAPR = 2,6-diaminopurine 2',3'-dideoxyriboside;
ddI = 2',3'-dideoxyinosine;
ddT = 2',3'-dideoxythymidine;
ddC = 2',3'-dideoxycytidine.

From the results shown in FIG. 1, the concentrations of nucleoside analog required to inhibit the virus replication by 50% ($ID_{50}$) are as follows: 0.07 µg/ml for 2,6 diaminopurine 2',3'-dideoxyriboside 0.07 µg/ml for 2',3'-dideoxyguanosine; 0.12 µg/ml for 2',3'-dideoxyadenosine; 1.5 µg/ml for 2',3'-dideoxyinosine and 40 µg/ml for 2',3'-dideoxycytidine. There was no inhibition of DHBV replication by 2',3'-dideoxythymidine.

EXAMPLE 1

Newborn ducklings are infected with DHBV. After 5 to 7 days post-infection, samples of blood are taken from the ducklings and examined for DHBV DNA using dot hybridization with a specific DNA probe [Mason et al, Proc. Natl. Acad. Sci. USA 79, 3997–4001 (1982)]. The livers are removed from dot-blot positive ducklings and used to produce primary hepatocyte cultures infected with DHBV as previously described. (Tuttleman et al, J. of Virology, 58, 17–25). After 2 days in culture, antiviral agents are added to the culture media. The media are changed every 2 days and at selected times, the cells are removed and the total DNA extracted.

Figure 2:
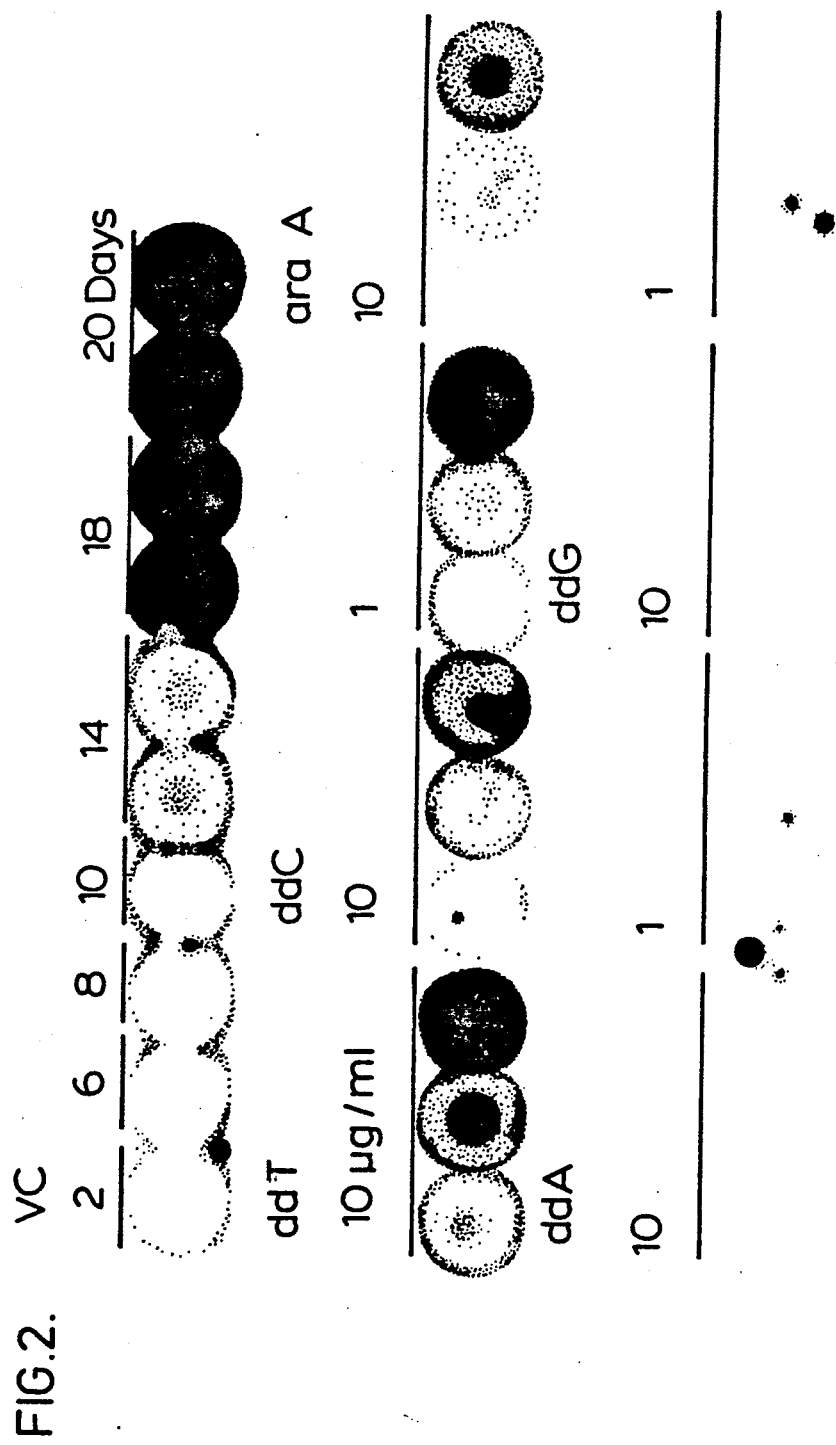
FIG. 2 is a dot blot hybridization of the DNA from virus control (VC) and drug-treated DHBV infected hepatocytes.

The DNA is spotted on nitrocellulose paper and probed with the $^{32}P$-labelled DHBV DNA probe in accordance with the following procedure. The DNA from DHBV-infected hepatocytes was extracted and spotted onto a nitrocellular filter. The above described $^{32}P$-nick translated—DHBV DNA (pDH—010=DHBV) probe was used. The DNA was extracted from 6-cm cell culture dishes at various times post-plating. In the VC group, cells were harvested at 2, 6, 8, 10, 14, 18 and 20 days. Duplicate samples were spotted for days 14, 18 and 20. In drug-treated groups, cells were harvested on days 8, 14 and 20. In FIG. 2, this is from left to right. Drugs were added to the culture at 2 days post-plating and maintained throughout media changes every 2 days. The concentrations (µg/ml) used are indicated in FIG. 2 for 2',3'-dideoxythymidine (ddT), 2',3'-dideoxycytidine (ddC), adenine arabinoside (ara A), 2',3'-dideoxyadenosine (ddA) and 2',3'-dideoxyguanosine (ddG). The total intracellular DNA was extracted from cells using the standard phenol extraction method. The cells in a 6-cm diameter Petri dish (approximately $5 \times 10^6$ cells) were lysed in a lysis buffer containing 0.2% SDS, 150 mM Tris-HCl pH 8.0, 10 mM EDTA, 5 mM EGTA, and 150 mM NaCl. The cell lysate was digested with 0.5 mg/ml of pronase E (available from Sigma) at 37° C. for 2 hours and deproteinized by extraction with an equal volume of phenol saturated with 20 mM Tris HCl, pH 7.5, 0.5 mM EDTA and 0.1% 8-hydroxyquinoline. Concentrated ammonium acetate [pH 7.0 (2.5 M)] was added to the aqueous phase to yield a 0.25 M ammonium acetate solution and the nucleic acids were precipitated with 2 volumes of 100% ethanol. The pellet of nucleic acid was washed with ethanol and dried. The DNA was dissolved in a solution containing 12.5 mM Tris HCl, pH 7.5, 10 mM EDTA, 30% glycerol and 0.01% bromophenol blue. One twelfth of the DNA sample was spotted onto the nitrocellulose for dot-blot analysis. ddA, ddG, ddC and ddT were purchased from Pharmacia. 2,6-Diaminopurine 2',3'-dideoxyriboside [or 2,6-diamino-9-2,3-dideoxy-β-D-glycero-pentofuranosyl)-purine] (ddDAPR) can be prepared by a procedure recently used for efficient conversion of adenosine into its ddAdo derivative (Robins et al, *Tetrahedron Lett.*, 25, 367–360, 1984; Hansske and Robins, *Tetrahedron Lett.*, 26, 4295–4298, 1985). Crystalline ddDAPR has mp 194° to 195° C.; MS m/z 250.1180 [M+ ($C_{10}H_{14}N_6O_7$)=250.1178].

This system demonstrates the unexpectedly high sensitivity of DHBV to 2′,3′-dideoxyadenosine (ddA) and 2′,3′-dideoxyguanosine (ddG). As shown in FIG. 2 2′,3′-dideoxythymidine (ddT) does not inhibit DHBV DNA synthesis even at a concentration of 10 μg/ml. 2′,3′-Dideoxycytidine inhibits the viral DNA production by approximately 57% at 10 μg/ml but has little inhibitory effect at 1 μg/ml. Adenine arabinoside at 10 μg/ml inhibits the DHBV-DNA synthesis by approximately 63%. However, both ddA and ddG inhibit DHBV-DNA synthesis by more than 99% at a concentration of 1 μg/ml. These results were consistent in triplicate experiments. See Table 2.

TABLE 2

Comparison of the Effectiveness of Purine 2,3′-dideoxynucleosides and pyrimidine dideoxynucleosides Inhibition of Hepadnavirus Replication
This is based on densitometry scans of the dot hybridization at 20 days.

| COMPARED | PERCENT INHIBITION |
|---|---|
| Media control | 0% |
| ddT (10 μg/ml) | 3% |
| ddC (1 μg/ml) | 0% |
| ddC (10 μg/ml) | 57% |
| araA (10 μg/ml) | 63% |
| ddA (10 μg/ml) | >99% |
| ddA (1 μg/ml) | >99% |
| ddG (10 μg/ml) | >99% |
| ddG (1 μg/ml) | >99% |
| 2,6-diaminopurine 2′,3′-dideoxyriboside (1 μg/ml) | 98%* |
| ddI (1 μg/ml) | 96%* |

*Dot hybridization for these two compounds not shown in FIG. 1.

EXAMPLE 2

Figure 3:
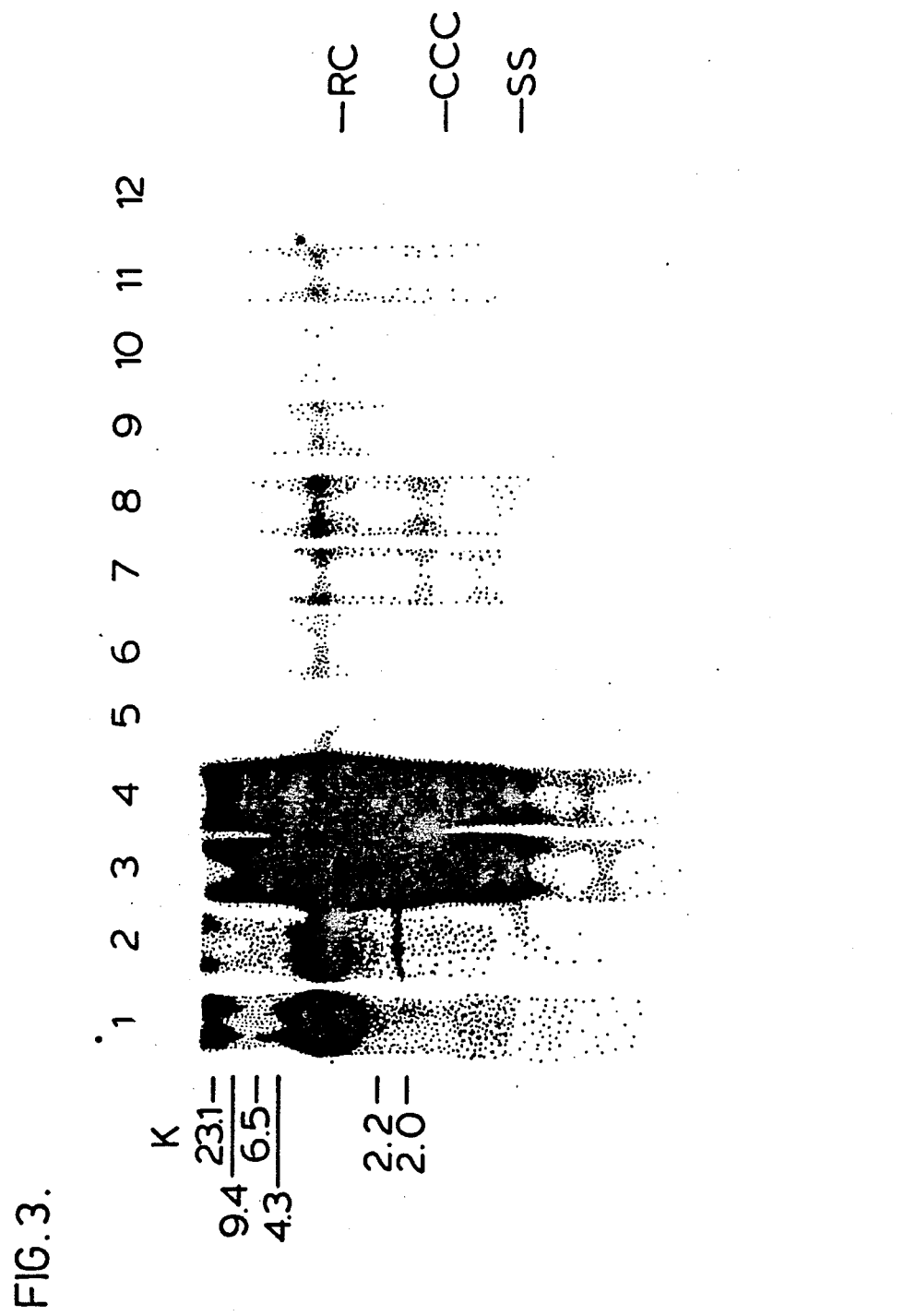
FIG. 3 is a Southern blot analysis of intracellular viral DNA separated on a 1.5% agarose gel.

Southern blot analysis confirms that the antiviral effect of the purine 2′,3′-dideoxynucleoside analogues is specific for DHBV DNA as shown in FIG. 3. This information was gathered as follows.

Southern blot analysis of intracellular viral DNA was separated on a 1.5% agarose gel. The DNA was extracted from DHBV-infected hepatocytes in a 6-cm dish and one fifth of the total DNA was applied onto each lane. As shown in FIG. 3, the virus control DNA was extracted at day 2 (lane 1), 8 (lane 2), 14 (lane 3) and 20 (lane 4). Drug-treated groups were harvested 14 and 20 days post-plating. The DNA samples from drug-treated hepatocytes were ddA (10 μg/ml), day 14 (lane 5) and day 20 (lane 6), ddA (1 μg/ml), day 14 (lane 7) and day 20 (lane 8), ddG (10 μg/ml), day 14 (lane 9) and day 20 (lane 10), ddG (1 μg/ml), day 14 (lane 11) and day 20 (lane 12). Relaxed circular (RC), covalently closed circular (CCC) and single-stranded (SS) DNA species are indicated in FIG. 3. The size markers (Kilobases) were obtained from HindIII digested bacteriophage λ DNA.

The relaxed circular (RC), covalently closed circular (CCC) any single stranded (SS) forms of DHBV DNA increase with incubation in the DHBV-infected hepatocytes. The synthesis of DHBV DNA is inhibited by ddA or ddG. However, in triplicate experiments ddG was more effective than ddA. There is very strong inhibition of the synthesis of all forms of DHBV DNA by ddA at a concentration of 1 μg/ml. There is a small increase in RC DNA in ddA treated hepatocytes from day 14 to day 20. On the other hand, ddG treatment results in a decrease in all forms of DHBV DNA by day 2.On the basis of these studies, ddG is a more effective antiviral agent for DHBV than ddA. However, both ddA and ddG are much more effective antiviral agents than ddC or ddT or other nucleoside analogues such as adenine arabinoside. Similar experiments using 2′,3′-dideoxyinosine (ddI) and 2,6-diaminopurine 2′,3′-dideoxyriboside (ddDAPR) have shown that these purine 2′,3′-dideoxynucleosides are also very effective antivirals for DHBV (>95% inhibition at 1 μg/ml). See Table 2. It is known that ddDAPR is deaminated by adenosine deaminase (Balzarini et al, *Biochem. Biophys. Res. Commun.* 145, 269–276, 1987; Balzarini et al, *Biochem. Biophys. Res. Commun.*, 145, 277–283, 1987). Therefore, it is likely that ddDAPR serves as an effective prodrug of ddG.

EXAMPLE 3

Figure 4:
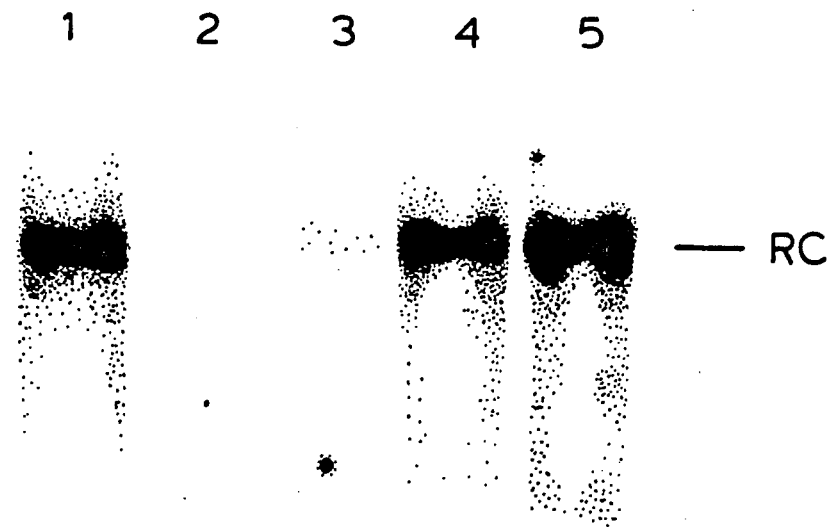
FIG. 4 is a Southern blot analysis of extracellular virion DNA separated on a 1.5% agarose gel.

The ability of the 2′,3′-dideoxynucleoside analogs to inhibit the production of extracellular DHBV is shown in FIG. 4. Southern blot analysis of the extracellular virion DNA was separated on a 1.5% agarose gel. Culture media were pooled from the day 16 to day 20 postplating. Pelleted virions were digested with pronase and the DNA from the entire sample, was applied to each lane. As shown in FIG. 4, virus control (lane 1), hepatocytes treated with 1 μg/ml of ddA (lane 2), hepatocytes treated with 1 μg/ml of ddG (lane 3), hepatocytes treated with 1 μg/ml of ddT (lane 4) and hepatocytes treated with 1 μg/ml of ddC (lane 5). RC in FIG. 4 indicated relaxed circular DNA.

The production of extracellular virus is markedly decreased by ddA or ddG at 1 μg/ml. However, ddT and ddC fail to inhibit the production of extracellular virus at 1 μg/ml.

Purine 2′,3′-dideoxynucleosides inhibit DHBV replication at low concentrations. The mechanism of selective inhibition of DHBV replication by the purine 2′,3′-dideoxynucleosides compared to pyrimidine 2′,3′-dideoxynucleosides is not known. However, as already noted, there is at least one possible explanation of the mechanism behind this discovery. Another possible mechanism is that the pyrimidine 2′,3′-dideoxynucleosides are not phosphorylated as effectively as purine 2′,3′-dideoxynucleosides in duck hepatocytes. However, even assuming very good phosphorylation of purine 2′,3′-dideoxynucleosides, the purine 2′3′-dideoxynucleoside triphosphates would have to compete with dGTP and dATP to inhibit viral DNA polymerase. The efficiency of the inhibition observed in these experiments suggests a unique mechanism of action for the purine 2′,3′-dideoxynucleosides. HBV should also be selectively inhibited by purine 2′,3′-dideoxynucleoside analogs. Based on the very similar mechanism of replication, HBV would show similar sensitivity to these antiviral agents. This method of treatment will prove effective against viruses that replicate in a similar manner to DHBV, for example, HBV in humans.

The 2′,3′-dideoxynucleoside analogs of Formula I may be administered as a biologically compatible ester, salt of such an ester or a biologically compatible salt. These compounds of the invention may be administered for therapy by one of several routes including oral, rectal, parenteral (intravenous, intramuscular or subcutaneous) or by aerosol inhalation.

It is known that purine 2',3'-dideoxynucleosides are susceptible to cleavage at acidic pH values such as those commonly found in the stomach. Therefore an oral formulation would be required that would bypass the acidic pH in the stomach. This may be accomplished by using a time-release capsule or by neutralization of the stomach pH before oral administration of the purine 2',3'-dideoxynucleosides.

For parenteral administration, the purine 2',3'-dideoxynucleosides would be in aqueous or non-aqueous sterile injectable solutions. Since these compounds are water soluable, an isotonic aqueous solution of neutral pH containing an appropriate buffer and an acceptable bacteriostatic agent would be the most likely formulation for intravenous administration.

It is desirable to obtain plasma levels of 1 to 10 $\mu$g/ml. In some circumstances, it is appreciated that higher levels may be required, although it is expected that levels of administration would not exceed 50 $\mu$g/ml in the blood stream.

Based on published studies of other 2',3'-dideoxynucleosides, the lower levels of 1 to 10 $\mu$g/ml can be readily achieved with the administration of 1-5 mg/kg by the oral route subject to the acidic lability limitations noted above. This is based on the known experience with other nucleoside analogues such as 3'-azido-3'deoxythymidine (AZT) which produces peak plasma levels of 1 $\mu$g/ml after infusions of 1 mg/kg or oral administration of 2 mg/kg. Similarly, effective plasma levels for the inhibition of HIV by ddC are achieved following oral administration.

The toxicity of the purine 2',3'-dideoxynucleosides has been tested in duck hepatocytes and monkey kidney cells (Vero) to reveal that decreased cell viability with ddA or ddG at 100 $\mu$g/ml over a 10 day exposure was not detected. As is known, several lymphocyte cell lines have been examined before for viability and function in the presence of 2',3'-dideoxynucleosides. These cell lines have not shown decreased viability and function in the presence of 2',3'-dideoxynucleosides. These cell lines have not shown decreased viability and only mildly suppressed immune function even when exposed to 100 $\mu$g/ml of 2',3'-dideoxynucleosides (Mitsuya et al *PNAS*, 82, 7096-7100, 1985).

EXAMPLE 4

Figure 5:
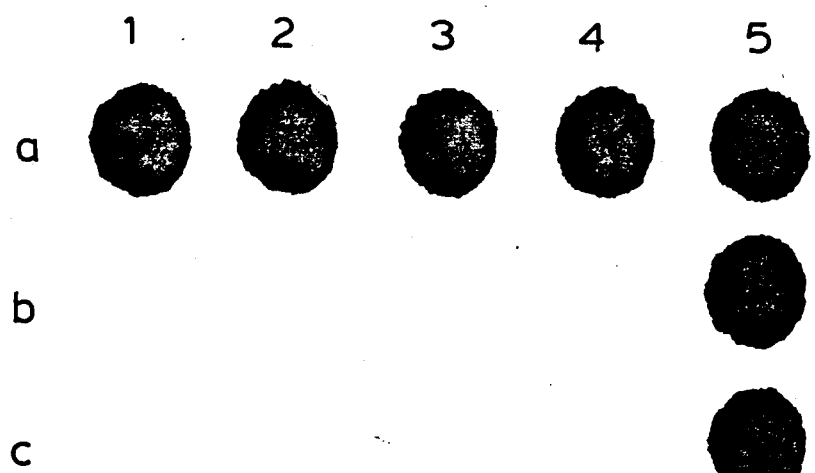
FIG. 5 is a dot blot analysis of sera extracted from animals infected with DHBV.

Additional tests were conducted to verify the activity in vivo. Four Pekin ducks with proven persistent infection with DHBV were treated with 2,6-diaminopurine 2',3'-dideoxyriboside (ddDAPR). The animals received 10 mg/kg twice daily by intramuscular injection for two weeks. The treatment resulted in very rapid clearance of the virus from the sera as shown in FIG. 5. Row "a" shows the dot-blot results of 5 animals prior to treatment. All five animals had evidence of persistent infection with DHBV. Animals 1 to 4 were treated and row "b" shows the results of treatment after 1 week. As can be seen, the treatment completely cleared the virus from their sera in one week. The untreated duck (number 5) was not bled at this time. Row "c" shows the dot-blot results after 2 weeks of treatment. The virus was cleared from the sera of the four treated ducks. The control animal (number 5) remained strongly positive after 2 weeks (row c, column 5).

We have also confirmed that ddDAPR is rapidly metabolized to ddG. This has been done using whole blood from a duck and measuring the rate of conversion of ddDAPR to ddG. Our results indicated that greater than 95% of the ddDAPR is metabolized to ddG in 5 minutes.

These tests provide striking confirmation that ddDAPR is very active in vivo as well as in vitro and is likely a prodrug of ddG.

Although preferred embodiments of the invention have been described herein in detail, it will be understood by those skilled in the art that variations may be made thereto without departing from the spirit of the invention or the scope of the appended claims.

The embodiments of the invention in which an exclusive property or privilege is claimed are defined as follows:

1. A method for medically treating an animal in need thereof and infected with a hepadnavirus, where said animal is susceptible to infection by said hepadnavirus, comprising administering to such animal a formulation comprising an efficacious amount of biologically active 2',3'-dideoxynucleoside in conjunction with a biologically compatible carrier, said 2',3'-dideoxynucleoside being represented by the formula:

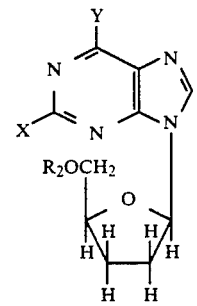

wherein X and Y are as follows:

|     | X    | Y                    |
| --- | ---- | -------------------- |
| 1.  | H    | OH                   |
| 2.  | H    | NH$_2$               |
| 3.  | NH$_2$ | OH                 |
| 4.  | NH$_2$ | OR(R=CH$_3$,C$_2$H$_5$) |
| 5.  | NH$_2$ | NH$_2$             |
| 6.  | NH$_2$ | H                  |
| 7.  | NH$_2$ | SH                 |
| 8.  | NH$_2$ | NHR(R=CH$_3$,C$_2$H$_5$) |
| 9.  | NH$_2$ | Halogen (F,Cl,Br,I) |
| 10. | NH$_2$ | SR(R=CH$_3$,C$_2$H$_5$) | and

R$_2$ is H or an acyl group having 1 to 4 carbon atoms which forms a biologically compatible ester or salt of said ester to provide a biologically compatible salt.

2. A method of claim 1 wherein said hepadnavirus is a hepatitis B virus.

3. A method of claim 1 wherein R$_2$ is H.

4. A method of claim 1, wherein R$_2$ is a biologically compatible ester.

5. A method of claim 3 wherein X is NH$_2$ and Y is OC$_2$H$_5$.

6. A method of claim 3 wherein X is NH$_2$ and Y is OH.

7. A method of claim 3 wherein X is H and Y is OH.

8. A method of claim 3 wherein X is NH$_2$ and Y is NH$_2$.

9. A method of claim 1, wherein said efficacious amount in an animal's bloodstream is less than 10 $\mu$g/ml.

10. A method of claim 9 wherein said efficacious amount in an animal's bloodstream is in the range of 0.1 to 10 μg/ml.

11. A method of claim 5 wherein said efficacious amount in an animal's bloodstream is in the range of 0.1 to 10 μg/ml.

12. A method of claim 6 wherein said efficacious amount in an animal's bloodstream is in the range of 0.1 to 10 μg/ml.

13. A method of claim 7 wherein said efficacious amount in an animal's bloodstream is in the range of 0.1 to 10 μg/ml.

14. A method of claim 8 wherein said efficacious amount in an animal's bloodstream is in the range of 0.1 to 10 μg/ml.

15. A method of claim 2 wherein said animal is a human.

16. A method of claim 11 wherein said hepadnavirus is hepatitis B virus.

17. A method of claim 12 wherein said hepadnavirus is hepatitis B virus.

18. A method of claim 13 wherein said hepadnavirus is hepatitis B virus.

19. A method of claim 14 wherein said hepadnavirus is hapatitis B virus.

20. A method of claim 16 wherein said formulation is in the form of an oral tablet, a liquid, a suppository, an injectable solution or an aerosol.

21. A method of claim 17 wherein said formulation is in the form of an oral tablet, a liquid, a suppository, an injectable solution or an aerosol.

22. A method of claim 18 wherein said formulation is in the form of an oral tablet, a liquid, a suppository, an injectable solution or an aerosol.

23. A method of claim 19 wherein said formulation is in the form of an oral tablet, a liquid, a suppository, an injectable solution or an aerosol.

24. A method of claim 1 wherein X and Y are as follows:

|     | X      | Y        |
|-----|--------|----------|
| 1.  | H      | OH       |
| 2.  | $NH_2$ | OH       |
| 3.  | $NH_2$ | $OCH_3$  |
| 4.  | $NH_2$ | $OC_2H_5$|
| 5.  | $NH_2$ | H        |
| 6.  | $NH_2$ | $NH_2$   |
| 7.  | $NH_2$ | $NHCH_3$ |
| 8.  | $NH_2$ | $NHC_2H_5$|
| 9.  | $NH_2$ | F        |
| 10. | $NH_2$ | Cl       |
| 11. | $NH_2$ | Br       |
| 12. | $NH_2$ | I.       |

25. A method of claim 24 wherein X is $NH_2$ and Y is $NH_2$.

26. A method of claim 24 wherein X is $NH_2$ and Y is OH.

27. A method of claim 24 wherein X is $NH_2$ and Y is $OCH_3$.

28. A method of claim 24 wherein X is $NH_2$ and Y is $OC_2H_5$.

29. A method of claim 24 wherein X is $NH_2$ and Y is $NHCH_3$.

30. A method of claim 24 wherein X is $NH_2$ and Y is Cl.

* * * * *